(12) United States Patent
Hatziavramidis (10) Patent No.: US 8,093,038 B2
(45) Date of Patent: Jan. 10, 2012

(54) APPARATUS AND METHOD FOR ENCAPSULATING PANCREATIC CELLS

(75) Inventor: Dimitri T. Hatziavramidis, Chicago, IL (US)

(73) Assignee: Illinois Institute of Technology, Chicago, IL (US)

( * ) Notice: Subject to any disclaimer, the term of this patent is extended or adjusted under 35 U.S.C. 154(b) by 1022 days.

(21) Appl. No.: 11/901,448

(22) Filed: Sep. 17, 2007

(65) Prior Publication Data
US 2009/0075359 A1 Mar. 19, 2009

(51) Int. Cl.
*A61K 9/14* (2006.01)
*A61K 9/16* (2006.01)
*A61K 9/50* (2006.01)
*C12M 1/00* (2006.01)
*C12N 5/00* (2006.01)
*C12N 5/02* (2006.01)

(52) U.S. Cl. .............. 435/283.1; 424/489; 424/490; 435/399; 435/403

(58) Field of Classification Search .................. None
See application file for complete search history.

(56) References Cited

U.S. PATENT DOCUMENTS

| | | | |
|---|---|---|---|
| 5,188,837 A | 2/1993 | Domb | |
| 5,871,767 A | 2/1999 | Dionne et al. | |
| 5,932,460 A | 8/1999 | Mills et al. | |
| 6,022,500 A | 2/2000 | John et al. | |
| 6,277,258 B1 | 8/2001 | Ivory et al. | |
| 6,537,829 B1 | 3/2003 | Zarling et al. | |
| 6,558,665 B1 | 5/2003 | Cohen et al. | |
| 6,558,952 B1 | 5/2003 | Parikh et al. | |
| 6,632,446 B1 | 10/2003 | Hubbell et al. | |
| 6,783,964 B2 | 8/2004 | Opara | |
| 6,911,227 B2 | 6/2005 | Hubbell et al. | |
| 6,993,383 B2 | 1/2006 | Assenheimer | |
| 7,022,313 B2 | 4/2006 | O'Connor et al. | |
| 7,079,244 B2 | 7/2006 | Gold et al. | |
| 7,128,931 B2 | 10/2006 | Leblond et al. | |
| 7,186,559 B2 | 3/2007 | Dzekunov et al. | |
| 2002/0058332 A1 | 5/2002 | Quake et al. | |
| 2002/0127144 A1 | 9/2002 | Mehta | |
| 2005/0214522 A1 | 9/2005 | Yukinobu et al. | |
| 2006/0127365 A1 | 6/2006 | Nurcombe et al. | |
| 2006/0268260 A1 | 11/2006 | Liu et al. | |
| 2007/0074182 A1 | 3/2007 | Hinchey et al. | |

FOREIGN PATENT DOCUMENTS

| | | |
|---|---|---|
| WO | WO 01/49407 A1 | 7/2001 |
| WO | WO 02/05944 A1 | 1/2002 |
| WO | WO 02/47665 A2 | 6/2002 |
| WO | WO 2004/002225 A1 | 1/2004 |
| WO | WO 2007/019845 A2 | 2/2007 |

OTHER PUBLICATIONS

Cohen, I. et al., Using Selective Withdrawal to Coat Microparticles, Science, 2001, vol. 292, pp. 265-267.
Lister, J.R., Selective withdrawal from a viscous two-layer system, J. Fluid Mech., 1989, vol. 198, pp. 231-254.
Rallison, J.M. et al., A numerical study of the deformation and burst of a viscous drop in an extensional flow, J. Fluid Mech., 1978, vol. 89, pp. 191-200.
Greener, Y., et al., A Theory of Roll Coating of Viscous and Viscoelastic Fluids, Polymer Engineering and Science, 1975, vol. 15, pp. 1-10.
Lee, G.B., et al., Hydrodynamic Focusing for a Micromachined Flow Cytometer, Transactions of the ASME, 2001, vol. 123, pp. 672-679.
Back, L.H., et al., Estimated Flow Resistance Increase in a Spiral Human Coronary Artery Segment, Journal of Biomechanical Engineering, 2000, vol. 122, pp. 675-680.
Wyman, J.L., et al., Immunoisolating Pancreatic Islets by Encapsulation with Selective Withdrawal, Small-Journal.com, 2007, vol. 3, No. 4, pp. 683-690.
Olsson, A., et al., Diffuser-element design investigation for valve-less pumps, Sensors and Actuators A, 1996, vol. 57, pp. 137-143.
Olsson, A., et al., A numerical design study of the valveless diffuser pump using a lumped-mass model, J. Micromech. Microeng., 1999, vol. 9, pp. 34-44.
Gerlach, T., Microdiffusers as dynamic passive valves for micropump applications, Sensors and Actuators A, 1998, vol. 69, pp. 181-191.
Yamahata, C., et al., Pumping of mammalian cells with a nozzle-diffuser micropump, Lab Chip, 2005, vol. 5, pp. 1083-1088.
Kizilel, S., et al., Sequential formation of covalently bonded hydrogel multilayers through surface initiated photopolymerization, Biomaterials, 2006, vol. 27, pp. 1209-1215.
Pan, L.S., et al., Analytical solutions for the dynamic analysis of a valveless micropump—a fluid—membrane coupling study, Sensors and Actuators A, 2001, vol. 93, pp. 173-181.
Li., S. et al., Analytical analysis of a circular PZT actuator for valveless micropumps, Sensors and Actuators A, 2003, vol. 104, pp. 151-161.
Fan, B., et al., Simulation of a piezoelectrically actuated valveless micropump, Smart Materials and Structures, 2005, vol. 14, pp. 400-405. Voisard, D., et al., Potential of Cell Retention Techniques for Large-Scale High-Density Perfusion Culture of Suspended Mammalian Cells, Biotech. Bioengineering, 2003, vol. 82, pp. 751-765.
Utada, A.S., et al., Monodisperse Double Emulsions Generated from a Microcapillary Device, Science, 2005, vol. 308, pp. 537-541.
Hatziavramidis, D., et al., Hydrodynamic analysis of pancreatic islet micro-encapsulation by selective withdrawal, Engineering Analysis with Boundary Elements, 2008, vol. 32, pp. 11-20.

*Primary Examiner* — Debbie K Ware
(74) *Attorney, Agent, or Firm* — Pauley Peterson & Erickson (57) ABSTRACT

An apparatus and method for coating micron-sized or sub-micron-sized particles such as living cells. The coating apparatus includes an encapsulation chamber enclosing a two-layer water-oil system for coating each islet cell with an aqueous polymeric coat. Islets together with an aqueous polymer solution are fed by a feed device that utilizes the principle of hydrodynamic focusing in order to ensure encapsulation of individual islets. The polymer in the aqueous coat is subsequently crosslinked by being exposed to laser light to produce structurally stable microcapsules of controllable thickness of the order of tens of microns. Encapsulated islets are removed from the encapsulation chamber by a valveless pump and recovered by filtration or centrifugation.

19 Claims, 5 Drawing Sheets

APPARATUS AND METHOD FOR ENCAPSULATING PANCREATIC CELLS

FIELD OF THE INVENTION

This invention relates generally to an apparatus and method for coating or encapsulating small particles, namely micro-sized particles and sub-micron particles, and, more particularly, to a device for encapsulation of living cells, e.g., pancreatic islet cells, intended for implantation into patients.

BACKGROUND OF THE INVENTION

More than one million people in the U.S. suffer from Type I diabetes, a disease in which pancreatic islets are no longer able to control glucose levels in the blood. The expectancy and quality of life of these patients is greatly compromised by diabetic complications that include retinopathies, renal failure, and vascular disease. An alternate therapeutic modality to regular insulin injections is transplantation of pancreatic islets from transgenic (allotransplantation) or nontransgenic (xenotransplantation) organisms. To suppress rejection by the recipient's immune system, transplanted islets are immunoisolated by enclosing them individually into microcapsules comprised of structurally stable, semipermeable membranes. The structural stability and selective permeability of the membrane ensures long-term viability and functionality of the islets.

Current methods for encapsulation generally include droplet generation, emulsion formation, polyelectrolyte multilayering, and direct polymerization from a surface-adsorbed initiator. Encapsulation methods are often restricted in terms of chemical composition, uniformity and thickness of the membrane, polymerization schemes, and applied stress to pancreatic islets. There is a need for an improved method for encapsulating islet cells.

SUMMARY OF THE INVENTION

A general object of the invention is to provide a cell encapsulation device with high yields of encapsulated pancreatic islets with long-term viability and functionality.

The general object of the invention can be attained, at least in part, through an apparatus for coating micron-sized or sub-micron-sized particles. The coating apparatus includes an encapsulation chamber including therein a first fluid layer of water or an aqueous solution disposed on a second fluid layer of a fluid incompatible with the first layer. The coating apparatus includes a particle feed tube with a particle passage in combination with a feed tube opening at a discharge end of the feed tube. The feed tube opening is disposed in the first fluid layer. A particle withdrawal tube includes a first end in combination with the encapsulation chamber and is connected at a second end to a filtration device.

The invention further comprehends an apparatus for coating micron-sized or sub-micron-sized particles. The coating apparatus includes an encapsulation chamber enclosing an aqueous fluid layer disposed on an oil fluid layer, and a particle feed device in combination with the encapsulation chamber by a particle feed tube. The particle feed tube includes a particle passage and a feed tube opening disposed in the aqueous fluid layer. The particle feed device includes a particle discharge channel having a particle discharge channel opening in combination with a first end of the particle passage. The particle feed device further includes a polymer solution injection channel adjacent the particle discharge channel and having an injection channel opening in combination with the first end of the particle passage. A particle withdrawal tube is connected at a first end to the encapsulation chamber and connected at a second end to a filtration device. A pump is in combination with the particle withdrawal tube.

The invention still further comprehends a method of coating micron-sized or sub-micron-sized particles. The method includes: mixing the particles with a polymer precursor solution in a particle feed tube; discharging the particles and the polymer precursor solution from the particle feed tube into an aqueous first fluid layer in an encapsulation chamber, the aqueous first fluid layer disposed on a second fluid layer formed of a fluid incompatible with the aqueous first fluid layer; removing the particles and at least a portion of the polymer precursor solution from the encapsulation chamber through a particle withdrawal tube; and polymerizing a polymer precursor of the polymer precursor solution within the particle withdrawal tube to coat the particles with a polymer material. Desirably, the mixing of the particles with a polymer precursor solution in the particle passage comprises hydrodynamically aligning the particles into a particle stream within the particle passage with at least one stream of the polymer precursor solution.

In one embodiment, removing the particles and at least a portion of the polymer precursor solution from the encapsulation chamber through a particle withdrawal tube comprises: placing an opening at an end of the particle withdrawal tube at a predetermined distance from an interface between the first fluid layer and the second fluid layer; drawing a stream of both the first fluid layer and the second fluid layer through the opening and into the particle withdrawal tube; and drawing the particles and the at least a portion of the polymer precursor solution through the opening and into the particle withdrawal tube.

The polymerization of the polymer precursor of the polymer precursor solution within the particle withdrawal tube to coat the particles with the polymer material includes applying light from a laser to the particles and the at least a portion of the polymer precursor solution within the particle withdrawal tube.

The device and method of this invention are particularly useful for encapsulation of pancreatic islet cells within a polymer film for implantation into patients suffering from Type I diabetes. The invention utilizes the method of selective withdrawal from a two-layer water-oil system for coating each islet with an aqueous polymeric coat. Islets together with an aqueous polymer solution are fed by the feed device that utilizes the principle of hydrodynamic focusing in order to ensure encapsulation of individual islets. The polymer in the aqueous coat is subsequently crosslinked by being exposed to laser light to produce structurally stable microcapsules of controllable thickness of the order of tens of microns. Encapsulated islets are removed from the encapsulation chamber by a valveless pump and recovered by filtration or centrifugation. The method and device of this invention ensure timely encapsulation of a number of islets, adequate for clinical trials, in microcapsules enclosed by semipermeable, hydrogel membranes of uniform thickness, that ensure long-term viability and functionality of the islets.

Other objects and advantages will be apparent to those skilled in the art from the following detailed description taken in conjunction with the appended claims and drawings.

DETAILED DESCRIPTION OF THE INVENTION

Figure 1:
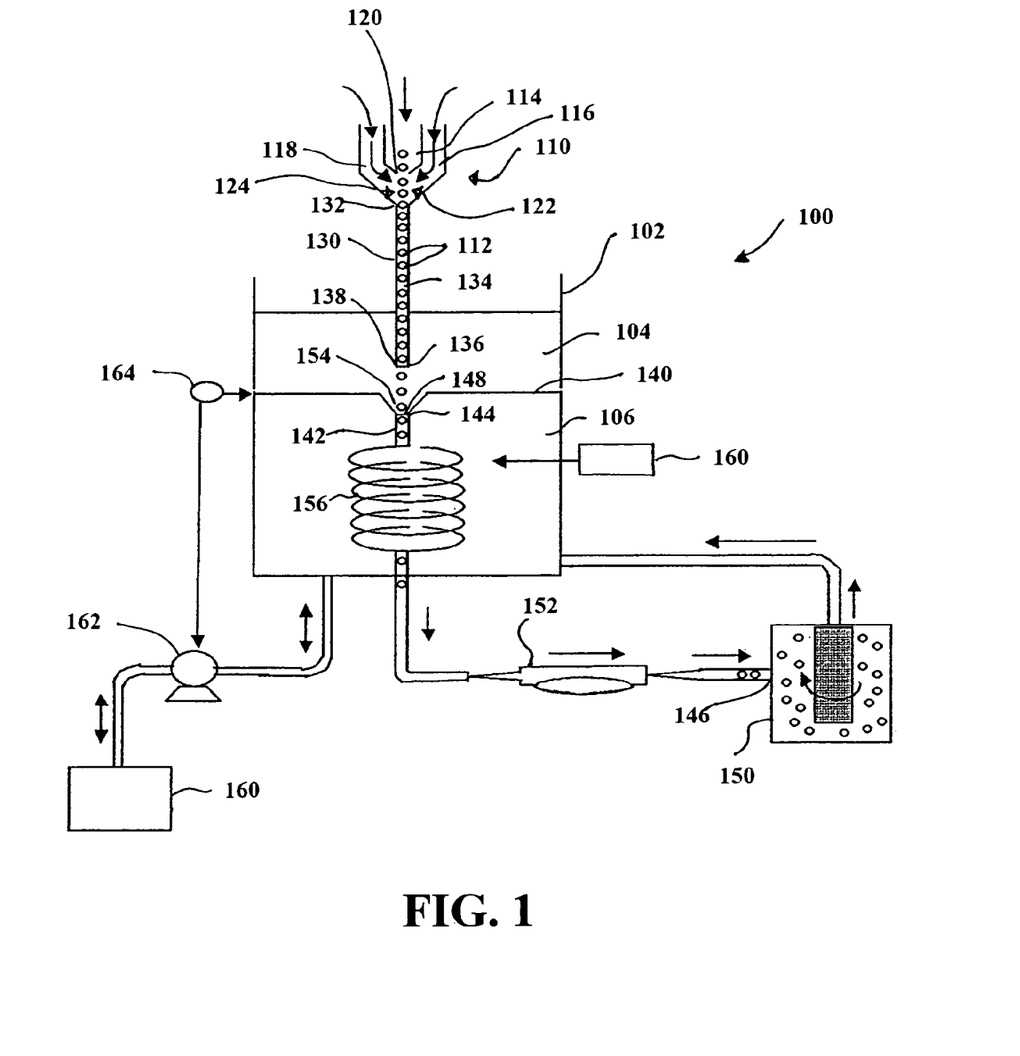
FIG. 1 illustrates a coating apparatus according to one embodiment of this invention.

FIG. 1 generally illustrates a coating apparatus 100 (not to scale) according to one embodiment of this invention for coating micron-sized or sub-micron-sized particles. The apparatus 100 includes an encapsulation chamber 102 with a first fluid layer 104 disposed on a second fluid layer 106. The second fluid layer 106 includes a liquid that is incompatible with the first fluid layer 104, thereby allowing the first fluid layer 104 to sit atop of the second fluid layer 106. In one embodiment of this invention the first fluid layer 104 includes water or an aqueous solution. The second fluid layer 106 can include any liquid that in incompatible with, and thus separates from, water, such as an oil. In one particularly preferred embodiment of this invention, the second fluid layer 106 includes a chlorinated hydrocarbon oil such as sold under the name PAROIL, available from Dover Chemical Corporation, Dover, Ohio.

A particle feed device 110 is in combination with the encapsulation chamber 102 so as to introduce thereto the particles 112 to be coated. The particles 112 can be any particles, but the apparatus of this invention is particularly suited for coating micron-sized particles and smaller. In one embodiment of this invention, the particles 112 are living cells or cell aggregates, and the invention will be described below with reference to pancreatic islet cells as the particles 112.

The particle feed device 110 shown in FIG. 1 includes a particle discharge channel 114 adjacent and between a first polymer solution injection channel 116 and a second polymer solution injection channel 118. The particle discharge channel includes a particle discharge channel opening 120 through which the islet cells 112 enter a particle passage 134 of a particle feed tube 130 at a feed tube first end 132. Each of the polymer solution injection channels 116 and 118 includes an injection channel opening 122 and 124 (respectively) in combination with the first end 132 and through which a polymer solution enters the particle passage 134 of the particle feed tube 130.

Figure 2:
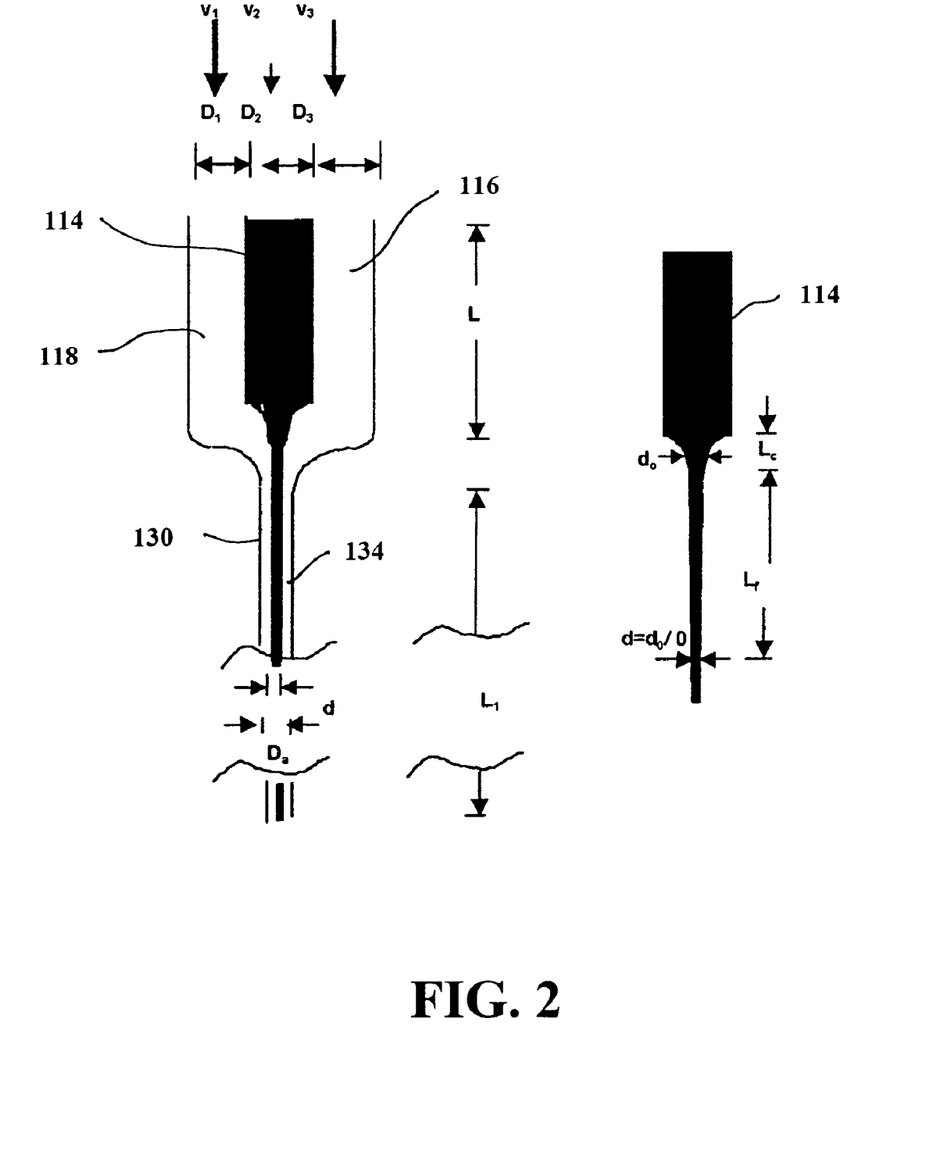
FIG. 2 is a schematic of a feed device for use in the coating apparatus on FIG. 1, according to one embodiment of this invention.

FIG. 2 is a schematic of the feed device 110, which is desirably constructed of a plastic such as poly(methyl methacrylate) (PMMA) material. The islets 112 are injected from the central particle discharge channel 114 and focused hydrodynamically into an aligned single-islet-file stream through the particle passage 134, constrained by polymer precursor solution flows from the two lateral injection channels 116 and 118. The feed device of FIG. 2 follows principles discussed in Lee et al., "Hydrodynamic Focusing for a Micromachined Flow Cytometer," Trans. ASME 123, 672 (2001), which are hereby incorporated by reference.

The polymer solution used in the particle coating apparatus of this invention can be any suitable polymeric solution for coating the cells 112. Desirably, the polymeric solution includes a precursor of the polymer intended to coat the islet cells 112. In one embodiment of this invention the aqueous polymeric solution for the coating material is contained in both the polymer solution injected through the injection channels 116 and 118 and in the aqueous first fluid layer 104. Examples of suitable polymers or polymer precursors include PEG-based polymers, such as PEG-diacrylate.

Referring again to FIG. 1, the particle feed tube 130 includes a feed tube opening 136 at a feed tube second end 138 that is opposite the first end 132. The feed tube opening 136 is disposed in the aqueous first fluid layer 104 at a predetermined distance above a fluid interface 140 (e.g., a water-oil interface).

A particle withdrawal tube 142 is in combination with the encapsulation chamber 102 and has a first end 144 disposed at a predetermined distance below the fluid interface 140. An opposing second end 146 of the particle withdrawal tube 142 is connected to a filtration device 150. A pump 152 is in combination with the particle withdrawal tube 142 upstream of the filtration device 150. The first end 144 includes a withdrawal tube opening 148 disposed within the second fluid layer 106.

The pump 152 withdraws oil through the particle withdrawal tube 142 at a rate that defines the flow as laminar. The flow rate is controlled to secure hydrodynamic stresses levels much below the critical stress that proves to be damaging to the living cells of the islets 112. If the withdrawal tube 142 is placed below the fluid interface 140 at a distance less than a critical distance, a thin spout 154 of the first fluid layer 104 is entrained with the oil. Islets 112 arriving at the fluid interface 140, by design, exactly above the opening 148 of the withdrawal tube 142, are drawn in the spout 154 and enter the withdrawal tube 142. Desirably, the islet 112 diameter is greater than a diameter of the spout 154 at the opening 148, so that the balance of interfacial and viscous forces causes the spout 154 to break both above and below the entrained islet 112. At this point, a thin layer of the aqueous polymeric solution surrounds the entrained islet 112 within the withdrawal tube 142. The polymeric solution with the islets 112 flows as a string of circular cross section, along the axis of the withdrawal tube 142, while the oil flows in the annulus between the tube wall and the lateral surface of the string.

After the islets 112 have been entrained into the withdrawal tube 142 and coated with the polymer solution, the islets 112 are exposed to light from a light source 160, such as, for example, 514 nm light of an argon-ion laser, that is in light discharge alignment with a portion of the withdrawal tube 142. The light source 160 is used to polymerize the polymer precursor within the polymer solution to coat the islets 112. In one embodiment of this invention the cell culture medium of islets 112 injected through particle discharge channel 114 and/or the polymer solution through injection channel 116 and/or 118 includes eosin-Y as a photoinitiator, 1-vinyl-2-pyrrolidinone as an accelerator and triethanolamine as a coinititiator for polymerization. The light excites eosin-Y and initiates free-radical polymerization to produce, for example, a poly(ethylene glycol) (PEG) hydrogel from a PEG-diacrylate precursor.

As shown in FIG. 1, the withdrawal tube 142 includes a coiled portion 156 which is used to provide sufficient time within the light beam for polymer crosslinking and hydrogel formation. As will be appreciated, the frictional pressure drop associated with the flow in the coiled part of the withdrawal tube is a function of the Dean number, which is nothing but the Reynolds number multiplied by the ratio of the tube-to-coil-curvature radii. Using the apparatus of this invention, the thickness of the resulting microcapsule shell enclosing an individual islet is controllable to within tens of a micron.

The coating apparatus 100 of FIG. 1 also includes an oil reservoir 160 connected to the encapsulation chamber 102 by a pump 162. A level sensor 164 measures the level of the second fluid layer 106 and the layer 106 is adjusted according to need to maintain the desired distance between the fluid interface 140 and the withdrawal tube 142.

FIGS. 3A-D illustrate features and operation of the pump 152. The pump 152 is a valveless diffuser-nozzle pump that has no interior mechanical parts for transporting mammalian cells with minimal and preferably no damage. The pump 152 is used to generate a selective withdrawal flow and remove the encapsulated islets 112 from the encapsulation chamber 102. The pump 152 is a diaphragm pump that uses two diffusers 170 and 172 as flow directing elements. The pump 152 is desirably made of a glassy plastic material (e.g., PMMA) with a flexible top portion 174 (e.g., poly(dimethyl acrylate) (PDMA)) over an internal fluid cavity. A piezoelectric (PZT) patch is bonded to the flexible top 174 of the pumping chamber, e.g., with epoxy resin, and is used in connection with applied AC voltage to set the three-layer (PZT-epoxy-PDMA) plate into vibration at a frequency, below the frequency of the natural frequency of the PDMA plate. The vibrating plate drives fluid flow, and at the same time, the fluid increases the resistance to the vibration (fluid flow and plate vibration are coupled). If the action of the fluid is negligible, the plate will vibrate at the same frequency as the piezoelectric (excitation) force for small amplitude vibrations.

Figure 3A:
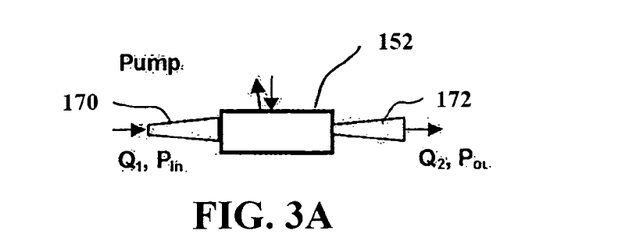
FIGS. 3A-D illustrate features and operation of the pump for use in the coating apparatus on FIG. 1, according to one embodiment of this invention.
Figure 3B:
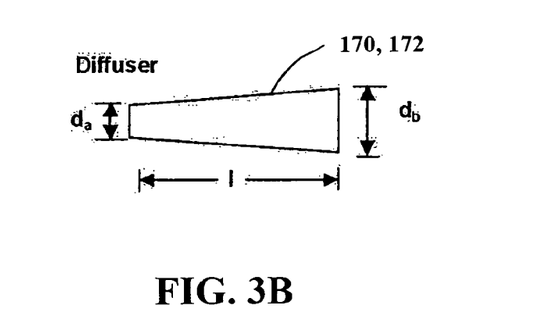
Figure 3C:
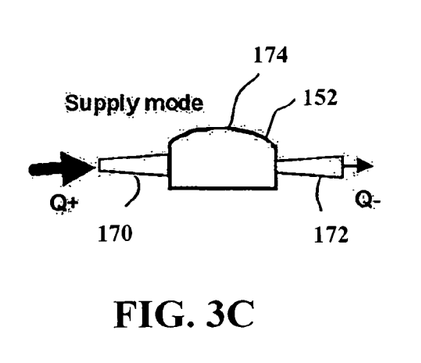
Figure 3D:
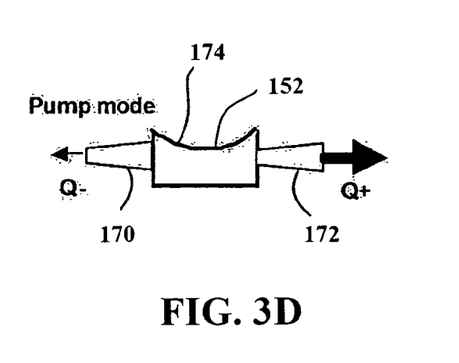

As shown in FIGS. 3C and 3D, the pump cycle can be divided into a supply and a pump mode. In the supply mode, the fluid cavity volume increases and a larger amount of the fluid flows into the cavity through the input element, i.e., diffuser 170, than through the output element, i.e., diffuser 172, which acts as a nozzle. In the pump mode, when the fluid cavity volume decreases, a larger amount of fluid flows out of the cavity through the output element 172, which acts as a diffuser, than the input element 170, which acts as a nozzle. The result for the complete pump cycle is that the net volume is transported from the input to the output side of the pump.

The ability of the valveless pump 152 to direct the flow in a preferential direction is measured by the rectification efficiency, $$\varepsilon = \frac{K_+ - K_-}{K_+ + K_-} = \frac{Q_+/|\Delta p| - Q_-/|\Delta p|}{Q_+/|\Delta p| + Q_-/|\Delta p|} = \frac{Q_+ - Q_-}{Q_+ + Q_-},$$

where the subscripts "+" and "−" refer to flow in the forward and backward directions. The rectification efficiency is, in turn, related to the efficiency of the nozzle-diffuser element, η, which is defined as the ratio of the total pressure loss coefficient in the nozzle direction to that for the flow in the diffusion direction, $$\eta = \frac{K_{n,t}}{K_{d,t}} = \frac{(K_{n,en} + K_n)(A_a^2/A_b^2) + K_{n,ex}}{K_{d,en} + K_d + K_{d,ex}(A_a^2/A_b^2)},$$

where the subscripts "t", "en", "ex" refer to total, entrance and exit, respectively, and $K_d$ and $K_n$ are the frictional loss coefficients in the "body" of the diffuser and nozzle, respectively.

The average flow rate through the pump 152 is given by $$\bar{Q} = \frac{1}{T}\int_0^T Q dt = \frac{K_n^{1/2} - K_d^{1/2}}{K_n^{1/2} + K_d^{1/2}} V_o \frac{\omega}{\pi},$$

where ω is the angular frequency of the applied electric field and $V_o$ is volumetric amplitude of the three-layer membrane.

Figure 5:
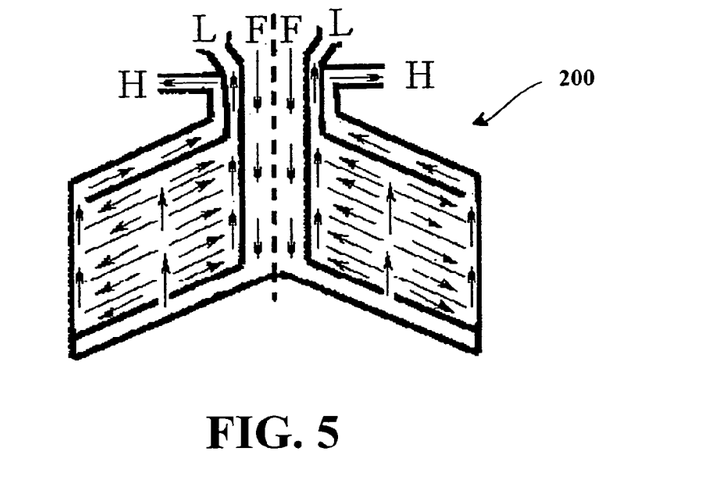
FIG. 5 illustrates the operation of a disk centrifuge for use in the coating apparatus on FIG. 1, according to one embodiment of this invention.

The encapsulated islets 112 are recovered in filtration device 150 shown in FIG. 1, for example, by mechanical filtration or centrifugation. High-retention filtration devices, e.g., spin-filters, can be utilized. Centrifugation can also be utilized, especially if it is desirable to recover the encapsulated islets 112 in a cell culture medium for the survival of islet cells. In this case, a buffer (aqueous) medium is desirably fed to the centrifuge simultaneously with the encapsulated-islets-containing oil, such as into a disk centrifuge 200 shown in FIG. 5. In FIG. 5, the feed solution F, which includes the oil, water and islets, is introduced into the disk centrifuge 200. The heavy phase H (oil) and light phase L (water) separate within the centrifuge and are pumped out, as indicated by the respective arrows. The encapsulated islets are then recovered in the cell culture medium, which comprises the light phase.

The present invention is described in further detail in connection with the following example which illustrates or simulates various aspects involved in the practice of the invention. It is to be understood that all changes that come within the spirit of the invention are desired to be protected and thus the invention is not to be construed as limited by these examples.

EXAMPLES

A coating apparatus according to FIG. 1 was constructed according to the following. All the parts of the coating apparatus, except for the top plate of the pumping chamber in the valveless pump, were made out of poly(methyl methacrylate) PMMA. The top plate of the pumping chamber was made out of poly(dimethyl acrylate). The particle feeding device for introducing, under hydrodynamic focusing, islets and precursor polymer solution was as shown in FIG. 2, with design parameters given in Table 1.

TABLE 1

| Hydrodynamic-Focusing Feed Device | |
|---|---|
| $v_a$ | 0.28 cm/s |
| $v_2 = \rho g D_2^2/32\mu$ | 21.26 cm/s |
| $D_a$ | 1.25 mm |
| d | 0.15 mm |
| $D_a/d$ | 8.35 |
| $v_1/v_2$ | 2.28 |
| $d_o$ | 1.5 mm |
| $d/d_o$ | 0.10 |
| $D_1 = D_2 = D_3$ | 2.63 mm |
| $L_f$ | 5.00 mm |
| $L_1$ | 29 cm |
| L | 3.125 mm |
| $L_e = 0.035 D Re$ | 0.52 cm |
| $L = L_e + 2$ | 2.52 cm |
| $L_c$ | 40 mm |
| $L_m = L_c/2$ | 20 mm |
| $v_1 = v_3$ | 48.51 cm/s |
| κ | 0.5 |
| Δp/ΔL | 16512.30 g cm$^{-2}$s$^{-2}$ |
| | 0.61 psi/in |
| Δp | 0.60 psi |
| ρgL | 2527.39 g cm$^{-1}$s$^{-2}$ |
| | 0.04 psi |
| Δp + ρgL | 0.64 psi |
| $Re_{1,3} = D_{1,3} * (1 - \kappa)v_1\rho/\mu$ | 63.88 <2000 ==> laminar |

The encapsulation chamber had a square cross section with 12.5 cm sides, and contained two fluid layers. Each layer had a height of 24 cm, on top of each other. The upper layer was an aqueous solution containing the polymeric precursor. The lower layer was PAROIL-152 (density of 1.26 g/cm$^3$), from Dover Chemical Corporation.

The feed tube of the particle feed device entered the aqueous layer and the feed tube opening was located at a distance of 7 mm above the water-oil interface. The islets, having an average diameter of about 150 µm, were fed at the rate of one islet per second and reached a terminal velocity of about 700 µm/s at about 0.03 µm below the feed tube opening. The opening of the lower part of the feed tube acted as a flow source. At equal distance, i.e., 7 mm, below the water-oil interface, an inlet opening of the withdrawal tube, having a diameter of 7.9 mm, acted as a flow sink of strength imposed by the valveless pump. Thus, the flow problem becomes selective withdrawal from a viscous two-layer system, with fluids of different viscosity in each layer, a source in the top layer and a sink of equal strength in the bottom layer and at equal distance on each side from the fluid-fluid interface.

The dimensionless sink strength, $Q=q\mu/(\rho_- g'h^4)$, where µ is the viscosity, $\rho_-$ the density of the lower layer, h the distance of the sink from the interface, and $g'=g(\rho_- -\rho_+)/\rho_+$, correlates with the capillary number, $\Gamma=\gamma/(\rho_- g'h^2)$. There is a critical value of the dimensionless sink strength, $Q_c$, such that for $Q>Q_c$, the interface is expected to be drawn into the sink and both fluids to be withdrawn. This analysis is correct for small disturbances of the interface toward the sink. Sufficiently large disturbances toward the sink will lead to simultaneous withdrawal, even if $Q<Q_c$. For the coating apparatus presented herein, $Q_c=0.54$ and $Q=0.10$ and, since $Q<Q_c$, subcritical equilibrium prevails.

If the interface is disturbed toward the sink, buoyancy and surface tension act as counteracting effects to the strain of the sink. When a source, is present in the upper layer, then the strain due to the source would be in such a direction as to augment the effects of the restoring forces (buoyancy and surface tension) and to stabilize the interfacial position. In the coating apparatus presented here, selective withdrawal occurs through a sink in the bottom layer, while a source in the upper layer feeds islets in a solution of polymer precursor.

A fluid drop of radius a in extensional flow of strain E will deform if $4\pi Ea/\Gamma>0.65$. In the selective withdrawal problem there is a stagnation point and extensional flow at the peak $(0, f(0))$ of any subcritical interfacial equilibrium. The tip of the interfacial peak is expected to behave in a manner analogous to the fluid drop. The equivalent criterion for instability is $2Qa/[\Gamma(1-f(0))^3]>0.65$, where a scales with the radius of the tip. This analysis applied to the coating device provides an estimate of the withdrawal tube diameter of approximately 8.0 mm (7.9 mm was used).

Figure 4:
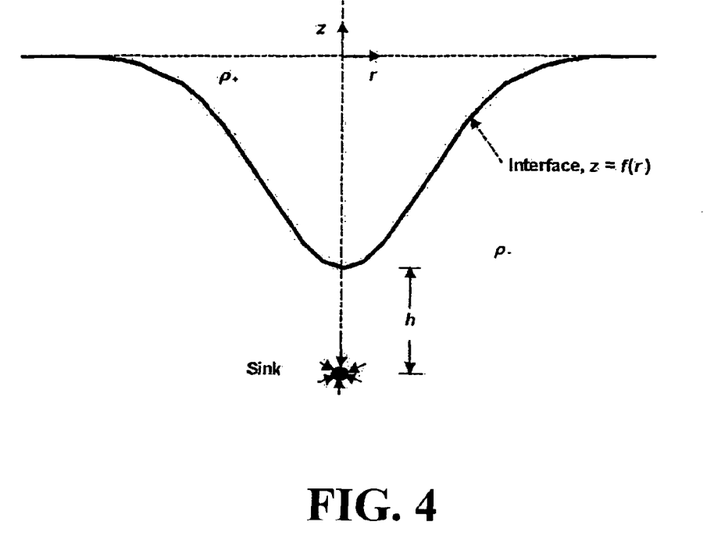
FIG. 4 illustrates the equilibrium position of the incompatible fluid interface, according to one embodiment of this invention.

The equilibrium position of the interface, $z=f(r)$, shown in FIG. 4, can be approximated asymptotically as $f \sim Qf_1+Q^2f_2+O(Q^3)$, with $f_1=(2-r^2)/[\pi(1+r^2)^{5/2}]$. The same quantity determined by numerical solution is slightly different from the estimate of the asymptotic solution, the difference being entirely due to the $O(Q^2)$ term. The upper-to-lower-fluid flux ratio, $\phi$, is estimated to be equal to 0.46, which for the withdrawal rate of 0.3 cm$^3$/s, results in average withdrawal velocities for the aqueous polymeric solution and the oil of 0.28 cm/s and 0.61 cm/s, respectively.

The withdrawal tube began as a straight vertical tube and included a coiled tube of length 190 cm, helix diameter 2.5 cm, and coil pitch of 2.4 cm. The pressure drop in the coiled part of the withdrawal tube, which is a function of the Dean number (i.e., Reynolds number multiplied by the square root of the ratio of the tube radius to the radius of curvature of the coil), was estimated to be 1.62 psi. A withdrawal rate of 0.3 cm$^3$/s was imposed on the system by a valveless diffuser/nozzle pump.

The characteristics of the nozzle-diffuser elements of the pump, electrical-mechanical coupling coefficient, $d_{31}$, layer thickness, h, Young modulus, E, Poisson ratio, v, are given below, where subscripts p, b and pzt refer to PDMS, bonding material, and PZT layer, respectively. With these properties, the resonance (natural) frequency of the pump actuator was estimated to be $f_1=850$ Hz.

TABLE 2

| Characteristics of nozzle-diffuser pump elements | |
|---|---|
| $d_{31}$ | 4.71E−10 m V$^{-1}$ |
| $h_p$ | 0.50 mm |
| $h_b$ | 0.02 mm |
| $h_{pzt}$ | 0.20 mm |
| $E_p$ | 4.9E+08 Pa |
| $E_b$ | 5.2E+09 Pa |
| $E_{pzt}$ | 1.6E+11 Pa |
| $v_p$ | 0.38 |
| $v_b$ | 0.30 |
| $v_{pzt}$ | 0.30 |

The diffuser and rectification efficiencies, η and ε, respectively, reach optimum values, for the desired withdrawal rate, when the length to diameter ratio of the diffuser, $l/d_a$, becomes equal to 25. The nozzle-diffuser pump elements characteristics are given in Table 3.

TABLE 3

| Nozzle-diffuser element characteristics and flow rates | |
|---|---|
| θ | 2.50° |
| $l/d_a$ | 25.00 |
| $d_a$ | 2.50 mm |
| $d_b$ | 7.96 mm |
| l | 62.50 mm |
| $K_{d,en}$ | 0.05 |
| $K_{d,ex}$ | 1.00 |
| $K_{n,en}$ | 0.40 mm |
| $K_{n,ex}$ | 1.00 |
| $K_d$ | 2017.23 |
| η | 7.85 |
| ε | 0.47 |
| $Q_+$ | 0.30 cm$^3$/s |
| $Q_-$ | 0.11 cm$^3$/s |
| $Q_+ + Q_-$ | 0.41 cm$^3$/s |

The volumetric amplitude, $V_o$, can be determined from the solution to the biharmonic equation for the deflection of the membrane. The deflection of the membrane, in turn, is a function of the excitation (piezoelectric) force or the potential of the electric field applied. The desired flow rate of 0.3 cm$^3$/s for this example was achieved with an AC electric field of potential 10V and a frequency of 90 Hz.

Figure 6:
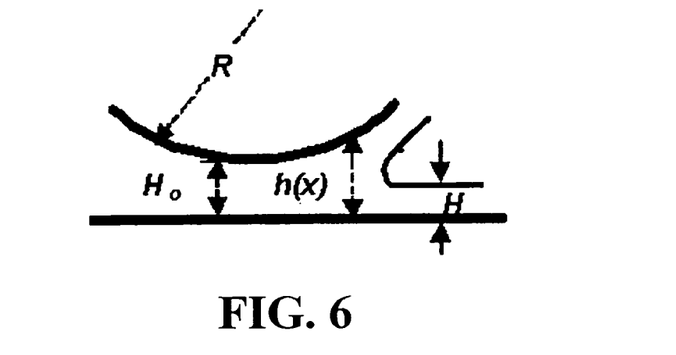
FIG. 6 illustrates a model of roll coating for determining a thickness of a encapsulating shell, according to one embodiment of this invention.

In evaluating the thickness of the obtained shell encapsulating the islets of this example, a model of roll coating as shown in FIG. 6 was utilized. For a viscous Newtonian fluid, the dimensionless thickness of the coating film is determined from an integral equation that contains the capillary number $$N_1 = \frac{\gamma}{\mu U}\left(\frac{H_o}{R}\right)^{1/2},$$

where γ is the surface tension, µ the viscosity of the fluid, U the average velocity of the fluid with regard to the roll (in this case particle), $H_o$ the minimum distance of the roll from the center of mass of fluid and R the radius of the roll (again, in this case particle). Using the aforementioned model, $H_o$=551 µm, $N_1$=1994 and the thickness of the coat of the pancreatic islets, of diameter 150 µm, is estimated to be 42 µm.

Thus, the invention provides a device and method for encapsulating particles, such as pancreatic islet cells for implants in patients with diabetes I. This device can be also used for coating other micron-size particles with a stable, crosslinked-polymer film of uniform and controllable thickness. However, it is particularly suitable for encapsulating living cells or cell aggregates, on an individual basis, i.e., one cell or one aggregate of cells per capsule. The obtained capsule shell is a stable, selectively permeable crosslinked-polymer membrane. Here, selectively permeable crosslinked-polymer membrane means that there is a cut-off size for species diffusing through the membrane, which correlates with the crosslinking density. The capsule shell thus produced provides immunoprotection to the living cells, when implanted, and ensures passage of cell nutrients and cell products, e.g., insulin and waste, to and from the interior of the capsule, respectively.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. An apparatus for coating micron-sized or sub-micron-sized particles, comprising:
    an encapsulation chamber including a first fluid layer of either water or an aqueous solution, the first fluid layer disposed on a second fluid layer of a fluid incompatible with the first layer;
    a particle feed tube including a particle passage in combination with a feed tube opening at a discharge end of the particle feed tube, the feed tube opening disposed in the first fluid layer;
    a particle feed device in communication with an end of the particle passage opposite the feed tube opening, the particle feed device comprising a particle discharge channel having a particle discharge channel opening in combination with the end of the particle passage, and a polymer solution injection channel having an injection channel opening in combination with the end of the particle passage;
    a particle withdrawal tube including a first end in combination with the encapsulation chamber and connected at a second end to a filtration device; and
    a valveless pump connected to the particle withdrawal tube between the first end and the second end.

2. The apparatus of claim 1, wherein the particles comprise living cells or cell aggregates.

3. The apparatus of claim 1, wherein the first fluid layer comprises an aqueous polymeric solution.

4. The apparatus of claim 3, wherein the fluid incompatible with the first layer comprises an oil.

5. The apparatus of claim 1, wherein the injection channel introduces a polymer precursor solution into the particle passage that hydrodynamically aligns the particles in the particle passage.

6. The apparatus of claim 1, further comprising a second polymer solution injection channel having a second injection channel opening in communication with the end of the particle passage.

7. The apparatus of claim 1, wherein the pump comprises a valveless diffuser-nozzle pump.

8. The apparatus of claim 1, wherein the particle withdrawal tube has a withdrawal tube opening at the first end and disposed within the second fluid layer.

9. The apparatus of claim 1, wherein the particle withdrawal tube comprises a coiled tube portion.

10. The apparatus of claim 1, further comprising a laser in light discharge alignment with a portion of the particle withdrawal tube.

11. A method of coating micron-sized or sub-micron-sized particles using the apparatus of claim 1, the method comprising:
    mixing the particles with a polymer precursor solution in the particle feed tube;
    discharging the particles and the polymer precursor solution from the particle feed tube into an aqueous first fluid layer in the encapsulation chamber, the aqueous first fluid layer disposed on the second fluid layer formed of the fluid incompatible with the aqueous first fluid layer;
    removing the particles and at least a portion of the polymer precursor solution from the encapsulation chamber through the particle withdrawal tube; and
    polymerizing a polymer precursor of the polymer precursor solution within the particle withdrawal tube to coat the particles with a polymer material.

12. The method of claim 11, wherein mixing the particles with the polymer precursor solution in the particle passage comprises hydrodynamically aligning the particles into a particle stream within the particle passage with at least one stream of the polymer precursor solution.

13. The method of claim 11, wherein removing the particles and at least a portion of the polymer precursor solution from the encapsulation chamber through a particle withdrawal tube comprises:
    placing an opening at an end of the particle withdrawal tube at a predetermined distance from an interface between the first fluid layer and the second fluid layer;
    drawing a stream of both the first fluid layer and the second fluid layer through the opening and into the particle withdrawal tube; and
    drawing the particles and the at least a portion of the polymer precursor solution through the opening and into the particle withdrawal tube.

14. The method of claim 11, wherein polymerizing the polymer precursor of the polymer precursor solution within the particle withdrawal tube to coat the particles with the polymer material comprises applying light from a laser to the particles and the at least a portion of the polymer precursor solution within the particle withdrawal tube.

15. An apparatus for coating micron-sized or sub-micron-sized particles, comprising:
    an encapsulation chamber enclosing an aqueous fluid layer disposed on an oil fluid layer;
    a continuous particle feed device in combination with the encapsulation chamber by a particle feed tube including a particle passage and a feed tube opening disposed in the aqueous fluid layer;

the particle feed device including a particle discharge channel having a particle discharge channel opening in combination with a first end of the particle passage, the particle feed device further including two polymer solution injection channels adjacent the particle discharge channel and each having an injection channel opening in combination with the first end of the particle passage;

a particle withdrawal tube connected at a first end to the encapsulation chamber and connected at a second end to a filtration device; and a valveless pump connected to the particle withdrawal tube between the first end and the second end.

16. The apparatus of claim 15, wherein the polymer solution injection channel introduces a polymeric precursor into the particle passage to hydrodynamically align the particles in the particle passage.

17. The apparatus of claim 15, wherein the oil comprises a chlorinated hydrocarbon oil.

18. The apparatus of claim 15, wherein the particle withdrawal tube comprises a coiled tube portion.

19. The apparatus of claim 15, further comprising a laser in light discharge alignment with a portion of the particle withdrawal tube.

* * * * *